(12) United States Patent
Kim et al.

(10) Patent No.: US 7,408,050 B2
(45) Date of Patent: Aug. 5, 2008

(54) MODIFIED CPG OLIGODEOXYNUCLEOTIDE WITH IMPROVED IMMUNOREGULATORY FUNCTION

(75) Inventors: Soo Kie Kim, Wonju-si (KR); Seung Kyu Park, Suwon-si (KR); Su Jung Park, Wonju-si (KR); Hyun Chul Cho, Wonju-si (KR)

(73) Assignee: Yonsei University, Seoul (KR)

( * ) Notice: Subject to any disclaimer, the term of this patent is extended or adjusted under 35 U.S.C. 154(b) by 504 days.

(21) Appl. No.: 10/920,181

(22) Filed: Aug. 18, 2004

(65) Prior Publication Data
US 2005/0152921 A1 Jul. 14, 2005

(30) Foreign Application Priority Data
Jan. 8, 2004 (KR) .................... 10-2004-0001161

(51) Int. Cl.
*C07H 21/02* (2006.01)
*A61K 51/00* (2006.01)
*A61K 47/00* (2006.01)
*A61K 39/00* (2006.01)

(52) U.S. Cl. .................... 536/23.1; 424/1.65; 424/278.1

(58) Field of Classification Search .................... None
See application file for complete search history.

(56) References Cited

U.S. PATENT DOCUMENTS

2005/0064401 A1* 3/2005 Olek et al. .................... 435/6

OTHER PUBLICATIONS

Kim et al., CpG-ODN-stimulated dendritic cells act as a potent adjuvant for E7 protein delivery to induce antigen-specific antitumour immunity in a HPV 16 E7-associated animal tumour model, 2004, Immunology, vol. 112, pp. 117-125.*
McCluskie et al., The potential of oligoeoxynucleotides as mucosal and parenteral adjuvants, 2001, Vaccine, vol. 19, pp. 2657-2660.*
Miconnet et al., CpG Are Efficient Adjuvants for Specific CTL Induction Against Tumor Antigen-Derived Peptide, 2002, The Journal of Immunology, vol. 168, pp. 1212-1218.*
Qin et al., CPG ODN Enhances Immunization Effects of Hepatitis B Vaccine in Agen Mice, 2004, Cellular and Molecular Immunology, vol. 1, No. 2, pp. 148-152.*
Glebe D., Recent advances in hepatitis B virus research: A German point of view, 2007, World Journal of Gastroenterology, vol. 13, No. 1, pp. 8-13.*
Zuckerman J., Vaccination against hepatitis A and B: developments, deployment and delusions, 2006, Current Opinions in Infectious Diseases, vol. 19, pp. 456-459.*
Vollmer J., Progress in drug development of immunostimulatory CpG oligonucleotide ligands for TLR9, 2005, Expert Opinion of Biological Therapies, vol. 5, No. 5, pp. 673-682.*
Bylund et al., Immunostimulatory DNA induces degranulation and NADPH-oxidase activation in human neutrophils while concomitantly inhibiting chemotaxis and phagocytosis, 2002, European Journal of Immunology, vol. 32, pp. 2847-2856.*
Pontarollo et al., Monocytes are required for optimum in vitro stimulation of bovine peripheral blood mononuclear cells by non-methylated CpG motifs, 2002, Veterinary Immunology and Immunopathology, vol. 84, pp. 43-59.*
A.M. Krieg, "CPG Motifs in Bacterial DNA and Their Immune Effects", Annu. Rev. Immunol., vol. 20, pp. 709-760, (2002).
D.M. Klinman et al., "CPG DNA: Recognition by and Activation of Monocytes", Microbes and Infection, vol. 4, pp. 897-901, (2002).
M. Gursel et al., "CPG Oligodeoxynucleotides Induce Human Monocytes to Mature Into Functional Dendritic Cells", Eur. J. Immunol., vol. 32, pp. 2617-2622, (2002).
H. Hemmi et al., "The Roles of Toll-Like Receptor 9, MYD88, and DNA-Dependent Protein Kinase Catalytic Subunit in the Effects of Two Distinct CPG DNAs on Dendritic Cell Subsets", The Journal of Immunology, vol. 170, pp. 3059-3064, (2003).
M. Kerkmann et al., "Activation With CPG-A and CPG-B Oligonucleotides Reveals Two Distinct Regulatory Pathways of Type I IFN Synthesis in Human Plasmacytoid Dendritic Cells", The Journal of Immunology, vol. 170, pp. 4465-4474, (2003).
B.V. Stern et al., "Vaccination With Tumor Peptide In CPG Adjuvant Protects Via IFN-$\gamma$-Dependent CD4 Cell Immunity", The Journal of Immunology, vol. 168, pp. 6099-6105, (2002).
Z.K. Ballas, "Divergent Therapeutic and Immunologic Effects of Oligodeoxynucleotides With Distinct CPG Motifs", The Journal of Immunology, vol. 167, pp. 4878-4886, (2001).
K. Heckelsmiller et al., "Peritumoral CPG DNA Elicits a Coordinated Response of CD8 T Cells and Innate Effectors to Cure Established Tumors in a Murine Colon Carcinoma Model", The Journal of Immunology, vol. 169, pp. 3892-3899, (2002).
J.E. Wooldridge et al., "Immunostimulatory Oligodeoxynucleotides Containing CPG Motifs Enhance the Efficacy of Monoclonal Antibody Therapy of Lymphoma", Blood, vol. 89, No. 8, pp. 2994-2998, (Apr. 15, 1997).
B. Jahrsdörfer et al., "Immunostimulatory CPG Oligodeoxynucleotides and Antibody Therapy of Cancer", Seminars in Oncology, vol. 30, No. 4, pp. 476-482, (Aug. 2003).
D.P. Sester, "Phosphorothioate Backbone Modification Modulates Macrophage Activation by CPG DNA", The Journal of Immunology, vol. 165, pp. 4165-4173, (2000).

* cited by examiner

*Primary Examiner*—Bruce Campell
*Assistant Examiner*—Benjamin P Blumel
(74) *Attorney, Agent, or Firm*—Finnegan, Henderson, Farabow, Garrett & Dunner, L.L.P.

(57) ABSTRACT

The present invention relates to a modified CpG oligodeoxynucleotide (ODN) which is prepared by coupling a consecutive sequence of deoxyribothymine (dT) to the 3'-terminus of CpG ODN having immunoregularory function, thereby improving immunoactivity of splenocytes, macrophages and peripheral mononuclear cells, and therefore, can be effectively used as a vaccine adjuvant for preventing and treating hepatitis B or an anti-cancer agent. Since the phosphorothioate CpG ODN having the consecutive sequence of dT at its 3'-terminus shows high activity inducing Th-1 immune response and does not elicit in vivo toxicity with guaranteeing its safety, it can be effectively used as a vaccine adjuvant.

7 Claims, 12 Drawing Sheets

SEQUENCE LISTING

```
<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: synthetic non-CpG oligonucleotide with no
      immunostimulatory effect

<400> SEQUENCE: 1
tccaggactt ctctcaggtt                                                 20

<210> SEQ ID NO 2
<211> LENGTH: 20
<212> TYPE: DNA
<213> ORGANISM: Artificial Sequence
<220> FEATURE:
<223> OTHER INFORMATION: synthetic CpG oligonucleotide with a
      phosphorothioate backbone effective especially on mice

<400> SEQUENCE: 2
tccatgacgt tcctgacgtt                                                 20

<210> SEQ ID NO 3
<211> LENGTH: 30
<212> TYPE: DNA
<213> ORGANISM: Artificial Sequence
<220> FEATURE:
<223> OTHER INFORMATION: synthetic CpG oligonucleotide with a
      phosphorothioate backbone and six guanines on 3'-terminal of
      KSK-12

<400> SEQUENCE: 3
tcgtcgtttt gtcgttttgt cgttgggggg                                      30

<210> SEQ ID NO 4
<211> LENGTH: 24
<212> TYPE: DNA
<213> ORGANISM: Artificial Sequence
<220> FEATURE:
<223> OTHER INFORMATION: synthetic CpG oligonucleotide with a
      phosphorothioate backbone effective especially on human

<400> SEQUENCE: 4
tcgtcgtttt gtcgttttgt cgtt                                            24
```

```
<210> SEQ ID NO 5
<211> LENGTH: 22
<212> TYPE: DNA
<213> ORGANISM: Artificial Sequence
<220> FEATURE:
<223> OTHER INFORMATION: synthetic CpG oligonucleotide with a
      phosphorothioate backbone

<400> SEQUENCE: 5
tcgtcgtttt cgtcgtcgtt tt                                              22
```

MODIFIED CPG OLIGODEOXYNUCLEOTIDE WITH IMPROVED IMMUNOREGULATORY FUNCTION

FIELD OF THE INVENTION

The present invention relates to a modified CpG oligodeoxynucleotide (ODN) with improved immunoregulatory functions. In particular, the present invention relates to the modified CpG ODN which is prepared by coupling a consecutive sequence of deoxyribothymine (dT) to the 3'-terminus of CpG ODN having immunoregularory function, leading to improved immunoactivity of splenocytes, macrophages and peripheral mononuclear cells, and therefore, can be effectively used as a vaccine adjuvant for preventing and treating hepatitis B or an anti-cancer agent.

BACKGROUND OF THE INVENTION

Vertebrate animals can suppress expression of CpG dinucleotide in their genomic DNA sequence or have a cytosine residue of the expressed CpG dinucleotide methylated (Krieg, *Ann. Rev. Immunol.*, 2002, 20, 709; McClelland & Ivarie, *Nucleic Acids Res.* 1982, 23, 78). Meanwhile, a microbial CpG dinucleotide is expressed at a normal rate and not methylated, and therefore it enables to detect microbial infection in vertebrates using the difference in the levels of the expressed CpG dinucleotide between vertebrate animals and microorganisms.

A microbial genomic DNA is recognized by dendritic cells or B cells expressing the TLR9 via toll-like receptor 9 (TLR9), a pattern recognition receptor, and eventually activates an innate immune system of a host cell. The innate immune system is endowed with a mechanism for removing cancer cells as well as a self defense mechanism against microbial or parasitic infections, and thus it is expected to develop a carcinostatic immunological adjuvant capable of inducing anti-cancer activity of an immune system by properly modifying the CpG ODN.

Studies for activating immune system using the CpG ODN have been actively progressed for the past few decades. The CpG ODN contains at least four bases at both 5'- and 3'-termini with reference to the CpG dinucleotide as the center, and immunoactivity of the CpG ODN is characterized by the base sequence. The CpG ODN is subdivided into two groups, K type and D type. K type ODN stimulates myeloid lineage cells and B cells thus resulting in their proliferation or secretion of immunoglobulin M or IL-6 (Klinman et al., *Microbes Infect.*, 2002, 897-901). On the other hand, D type ODN activates monocytes to be differentiated into dendritic cells or stimulates natural killer cells to secrete IL-6 (Klinman et al., *Eur. J. Immunol.*, 2002, 32, 2617-22; Gursel et al., *J. Leukoc. Biol.*, 71, 813-20, 2002). Further, the D type ODN activates B220$^+$ dendritic cells to produce IFN-α while TLR9$^+$ B220$^+$ dendritic cells release IL-12 in response to D type ODN. These results suggest that there might be several pathways to improve immune activity of the CpG ODN by stimulating specific immunocytes (Hemmi et al., *J. Immunol.*, 2003, 170, 3059-3064; Kerkman et al., *J. Immunol.*, 2003, 170, 4465-4474).

Various types of CpG ODNs have been designed to redirect the pathologic condition such as infection, autoimmune disease and cancer. Of these, the strategy toward the development of immunotherapeutic CpG ODN against cancer can rely upon effector cells mainly stimulated by CpG ODN. To augment cell-mediated immunity using CpG ODN, the following two methods are commonly exploited.

The first method is to augment a local or systemic immunity via an activation of naive or professional dendritic cells. Cancer cells down-regulate their antigen presentation capabilities to escape an immune surveillance system of a host cell, thereby enabling to survive in the host cell taking advantage of the fact that host cytotoxic T cells are unable to recognize them. To solve this problem, there has been developed a method that immunizes a host with a strong immunogenic peptide in a cancer antigen together with the CpG ODN as an immune adjuvant. By this method, the dendritic cells with high antigen presentation activity can uptake the peptide of cancer antigen and when activated by the CpG ODN, leading to activating cytotoxic T cells. The activated cytotoxic T cells can then effectively eliminate the cancer cells. It has been reported that this method can kill RMA from a mouse (Stern et al., *J. Immunol.*, 2002, 168, 6099-6105). IFN-γ plays an important role in these immune responses. Although this is not done through activation of dendritic cells, it still enables to activate anti-cancer immunity same as in the mechanism of dendritic cells by rendering CpG ODN 2006 to directly work on B cells as well as to increase the expression of a costimulator which can induce an interaction between B and T cells (Jahrsdorfer et al., *J. Leukoc. Biol.*, 2001, 69, 81-88).

The other method is to augment innate immunity via activation of natural killer cells. It is possible to activate cytotoxic T cells by activating dendritic cells by introducing a cancer antigen from the outside, but it is essential to present the cancer antigen on the surface of MHC class I molecule for eliciting cytotoxicity from cytotoxic T cells. However, in many cases the level of presenting caner antigens on the surface of cancer cells is too low to elicit cytotoxicity from cytotoxic T cells, and therefore the method for removing cancer cells by activating the dendritic cells often becomes ineffective. To overcome this limitation, it has been suggested to activate natural killer cells which exert cytotoxicity regardless of cancer antigen presentation on the surface of a cancer cell. Further, the activated natural killer cells activate monocytes or macrophages, leading to activation of antigen-independent anti-cancer immune system. It has been reported that CpG ODN 1584 administration in vivo blocks the metastasis of NK sensitive B16.F1 melanoma whereas CpG ODN 1826 injection effectively rejects NK resistant EL4 lymphoma in an in vivo_mouse tumor model using the above method (Ballas et al., *J. Immunol.*, 2001, 167, 4878-4886). Further, when ODN 1826 was directly injected into a tumorigenic lesion after induction of C26 colon carcinoma mass in BALB/C mice, the size of the tumor was markedly decreased. This data shows that peritumoral CpG ODN monotherapy elicits a strong CD8 T cell response and innate effector mechanisms that seem to act in concert to overcome unresponsiveness of the immune system toward a growing tumor. (Heckelsmiller et al., *J. Immunol.*, 2002, 169, 3892-3899). In contrast, it is difficult to eliminate the murine 38C13 B cell lymphoma in vivo by means of CpG ODN monotherapy. However, if a monoclonal antibody specific to 38C13 lymphoma antigen is treated with the CpG ODN, the activated natural killer cell is capable of efficiently removing 38C13 lymphoma by exerting antibody-dependent cell cytotoxicity (Woodridge et al., *Blood*, 1997, 89, 2994-2998).

Meanwhile, humoral immunity against cancer can be induced by using an antigen or an equivalent thereof together with the CpG ODN as an immunostimulant. Trastuzumab and rituximab have been known as commercial monoclonal antibodies specific to HER-2 protein over-expressing cancer cell and non-Hodgkins B cell lymphoma, respectively. Recently, the combination therapy with the CpG ODN plus tumor antigen specific antibody demonstrated the potent tumor rejection preclinically and is now entering into clinical trials. (Jahrsdorfer et al., *Sem. Oncol.*, 2003, 30, 476-482).

The CpG ODN has strong innate immunoactivity due to the nucleotide sequences containing CpG dinucleotides present at 5'- and 3'-termini. However, since the CpG ODN itself is of a wild-type structure having no difference from a structure of in vivo DNA molecule, it does not show any cytotoxicity. However, there is a disadvantage in the CpG ODN that it is easily degraded in vivo due to its wild-type structure, consequently leading to reducing half-life of immunoactivity. Although it is possible to increase a daily dosage of CpG ODN to overcome this drawback, it is not economical. It has been reported that when a phosphodiester bond known as a backbone of DNA molecule is changed into a phosphorothioate bond during the synthesis of CpG ODN, immunoactivity of the CpG ODN is amplified about 10 to 100-folds (Sester et al., *J. Immunol.*, 2000, 165, 4165-4173). However, this method has the problems of bringing about cytotoxic effects to immune cells as well as changes in immunoactivity of the CpG due to a modification in backbone. Therefore, it is unclear whether this method would be optimal to structural modification of CpG ODNs.

The CpG ODN shows species-specificity and there has been no report that the CpG ODN shows a high immunoactivity in humans comparable to that it has shown in experimental animals. Further, since the action mechanism of CpG ODN is still unknown, it is hard to develop potent immunotherapeutic CpG ODN to target human immune cells. Consequently, there is very rare CpG ODN for a clinical trial. These limitations necessitate the development of CpG ODN either with superior immune-stimulating activity or lower side effects comparing to the existent CpG ODN.

The present inventors devised the simple method to solve the above problems. That is, a modified CpG ODN was prepared by coupling a consecutive sequence of deoxyribothymine (dT) to the 3'-terminus of CpG ODN, thus improving immunoactivity of splenocytes, macrophages and peripheral mononuclear cells, and therefore, can be effectively used as a vaccine adjuvant for preventing and treating hepatitis B or an anti-cancer agent.

SUMMARY OF THE INVENTION

Accordingly, an object of the present invention is to provide a modified CpG ODN having an improved immunoregulatory function.

Another object of the present invention is to provide a vaccine adjuvant or an anti-cancer agent comprising a modified CpG ODN as an effective ingredient.

BRIEF DESCRIPTION OF THE DRAWINGS

The above and other objects and features of the present invention will become apparent from the following description of the invention, when taken in conjunction with the accompanying drawings, wherein.

| M: maker; | 1: no treatment; |
|---|---|
| 2: 0.6 µg/ml KSK-1; | 3: 0.6 µg/ml KSK-2; |
| 4: 0.6 µg/ml KSK-7; | 5: 0.6 µg/ml KSK-12; |
| 6: 0.6 µg/ml KSK-13; | 7: 0.1 µg/ml LPS |

Figure 3A:
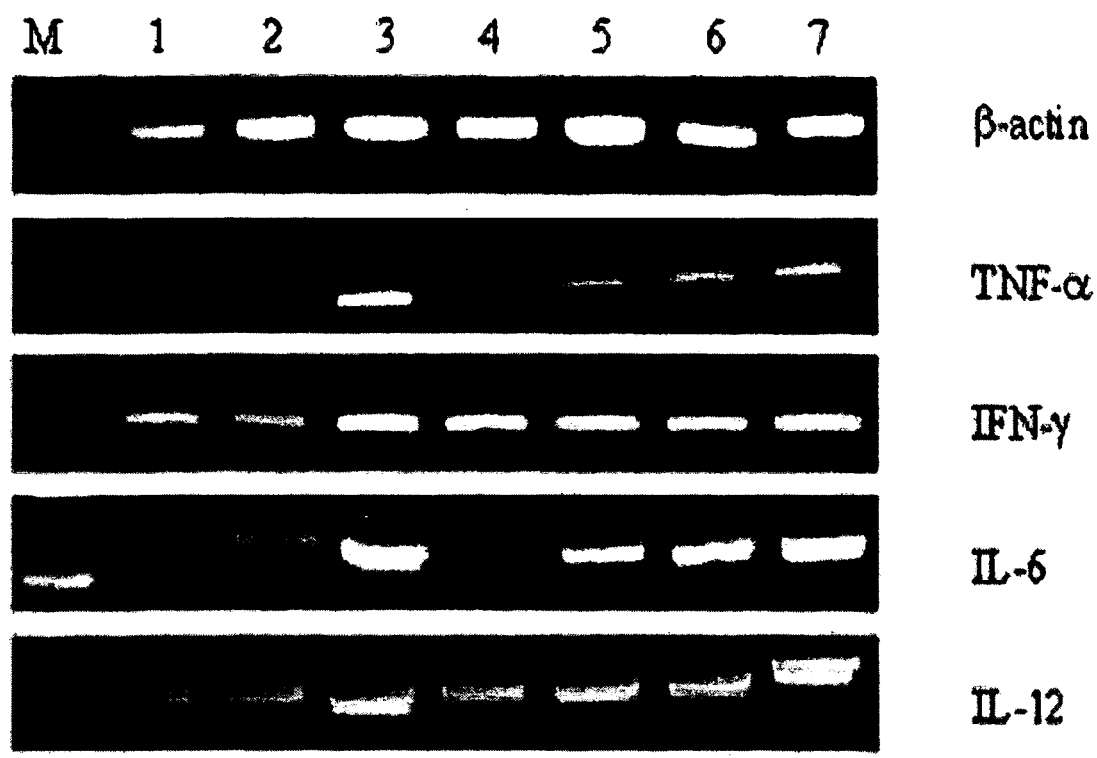
Figure 3B:
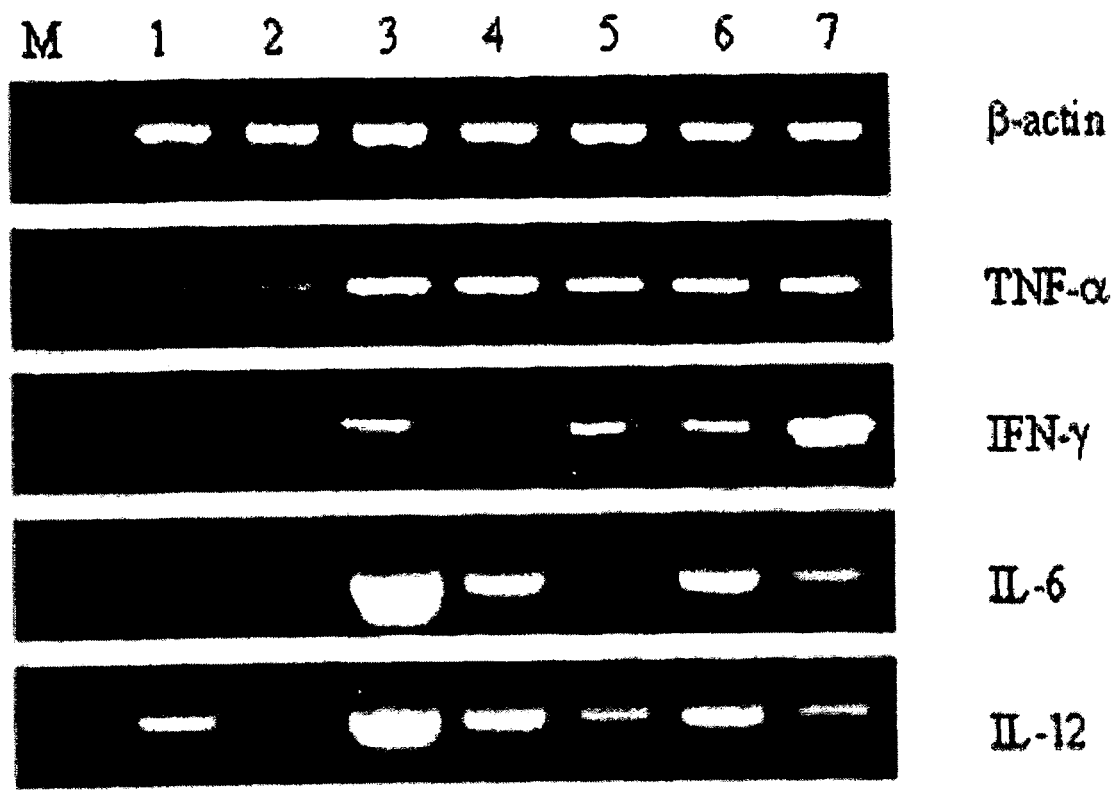

FIG. 3a shows the results of examining whether the CpG ODN of the present invention induces expression of Th1 type cytokine mRNA of BALB/C mouse splenocytes in vitro;

FIG. 3b shows the results of examining whether the CpG ODN of the present invention induces expression of Th1 type cytokine mRNA of BALB/C mouse splenocytes in vivo;

| M: marker; | 1: 0.6 µg/ml CpG ODN; |
|---|---|
| 2: 0.6 µg/ml KSK-1; | 3: 0.6 µg/ml KSK-2; |
| 4: 0.6 µg/ml KSK-7; | 5: 0.6 µg/ml KSK-12; |
| 6: 0.6 µg/ml KSK-13; | 7: 0.1 µg/ml LPS |

Figure 4A:
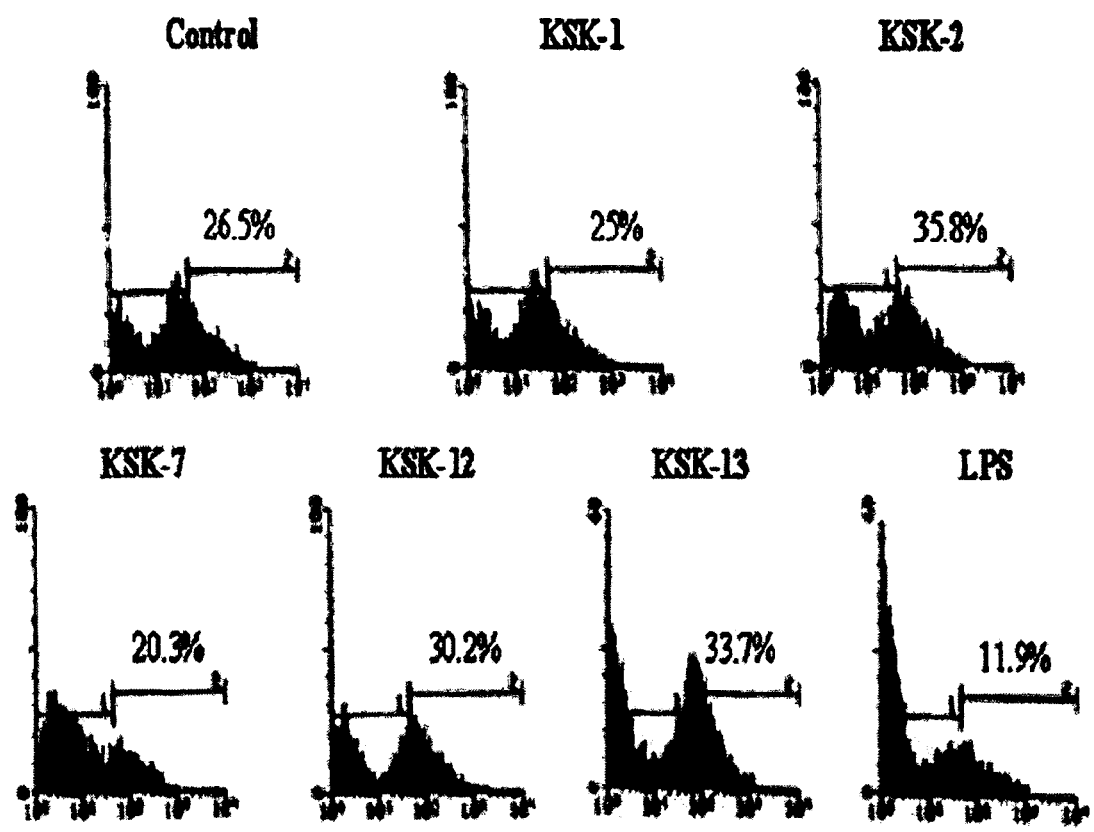
Figure 4B:
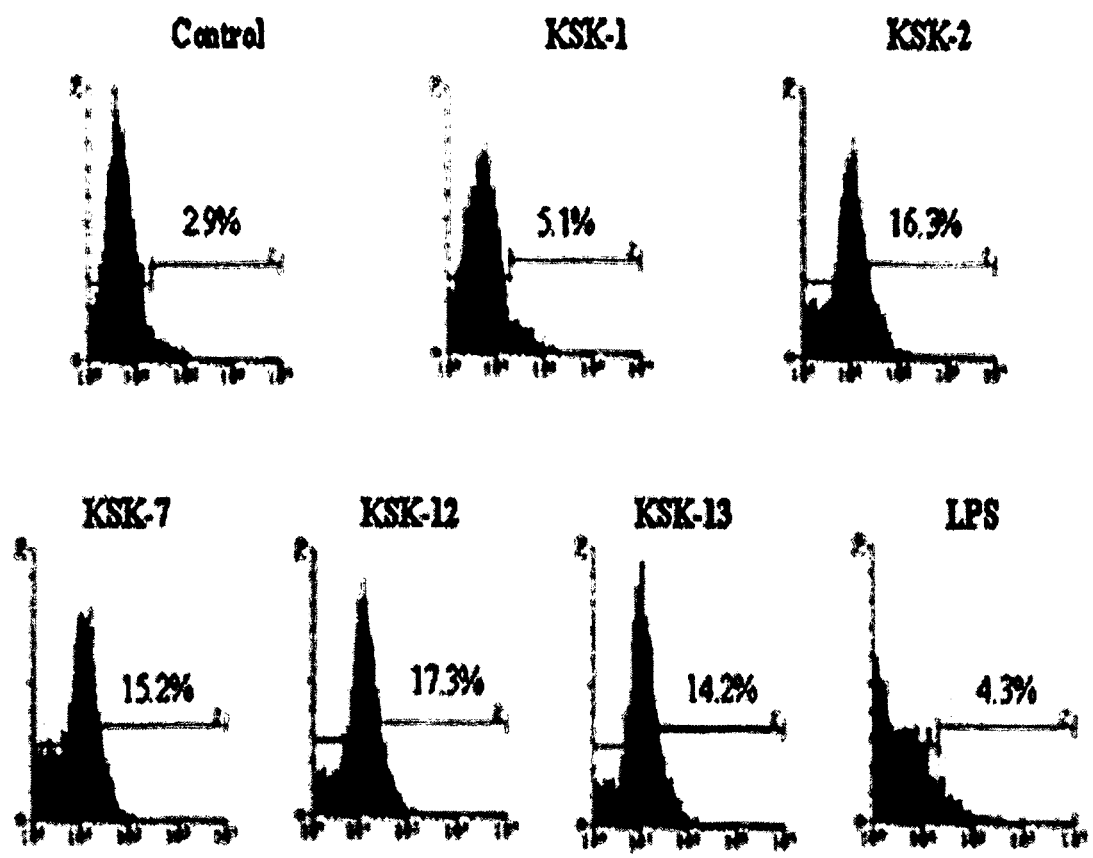
Figure 5A:
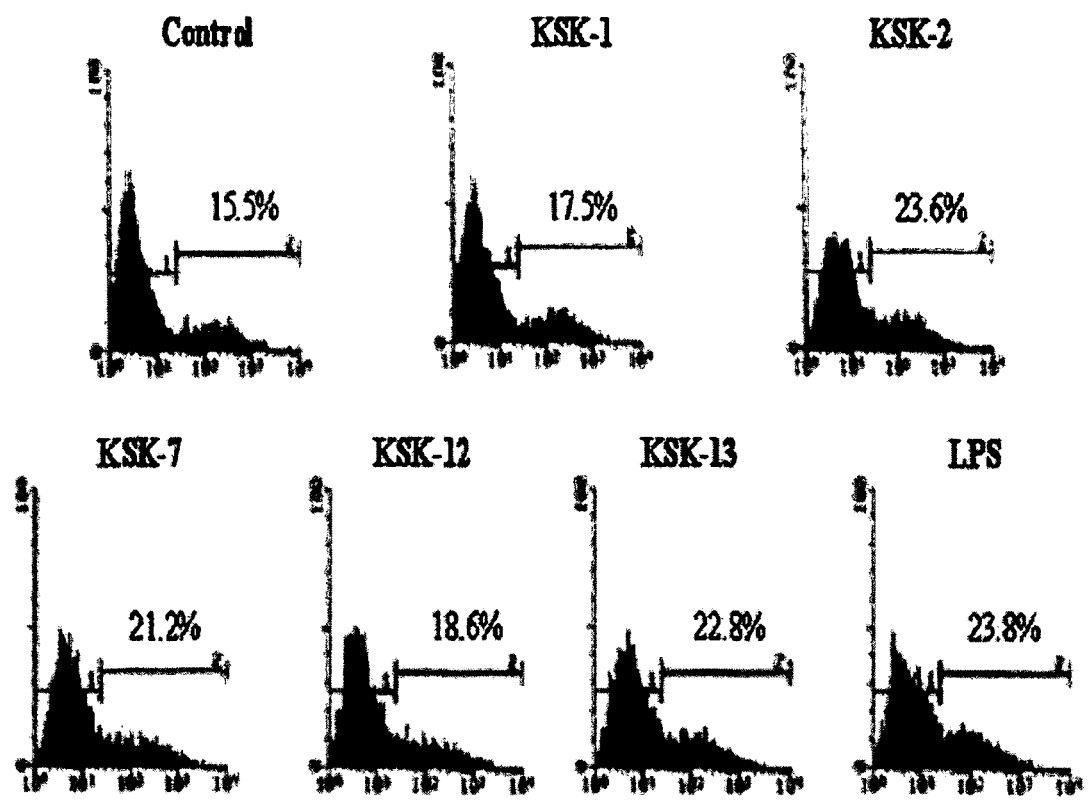
Figure 5B:
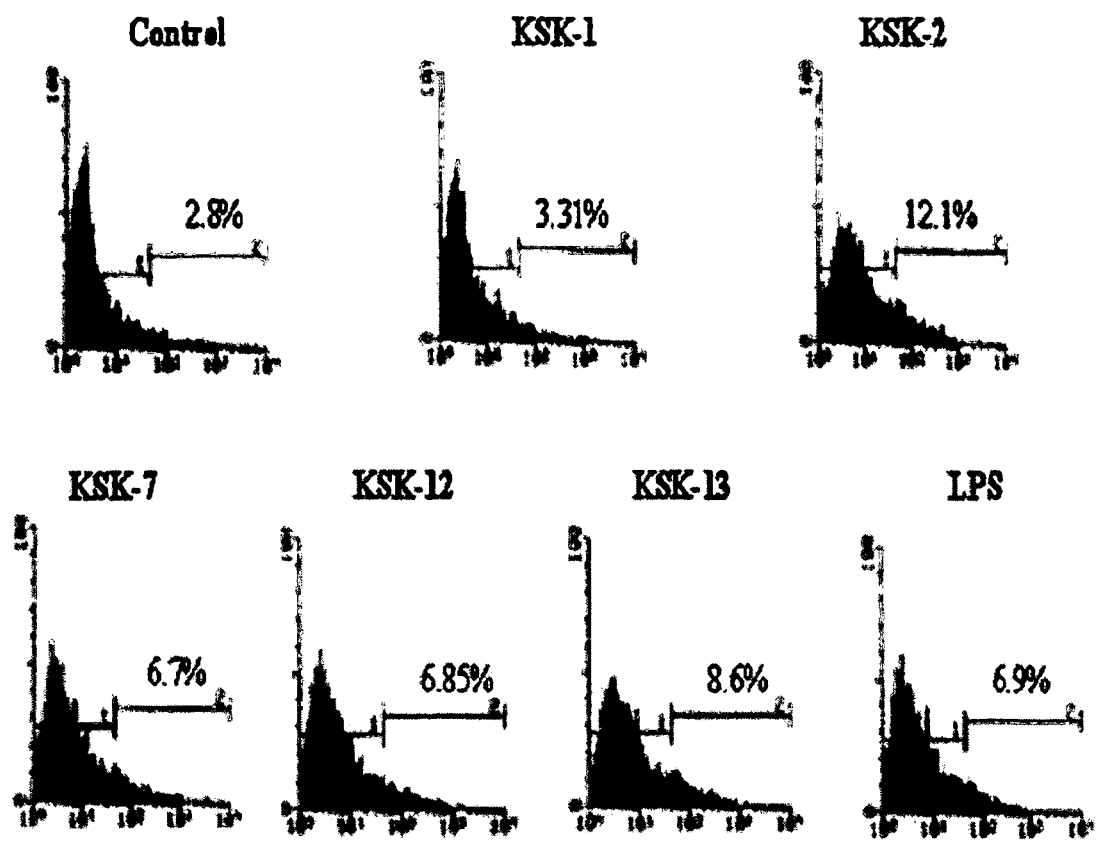
Figure 6A:
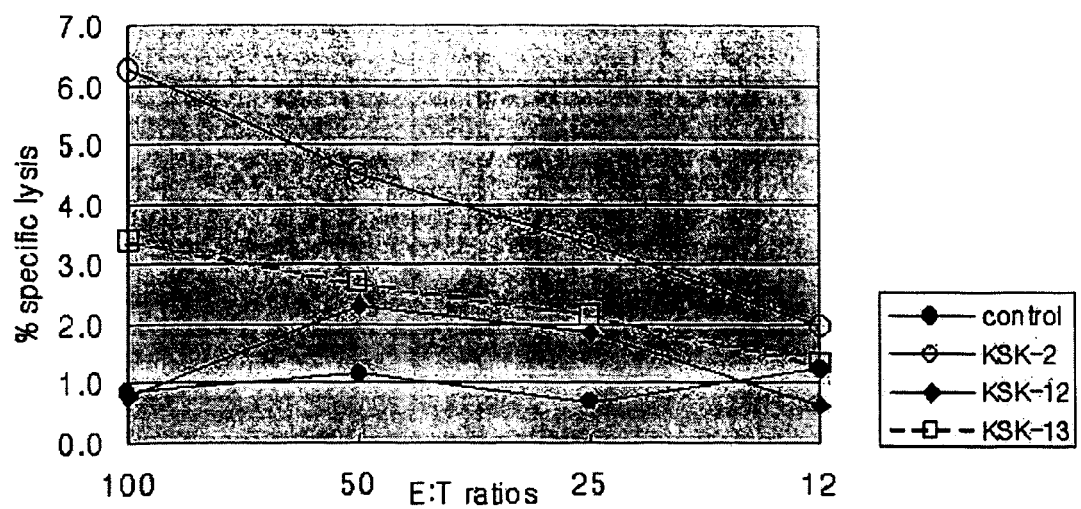
Figure 6B:
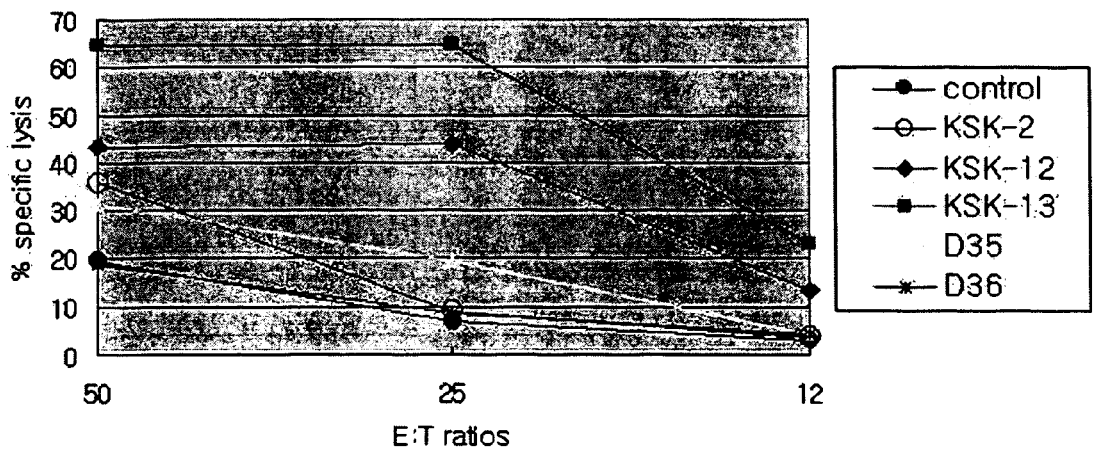
Figure 7:
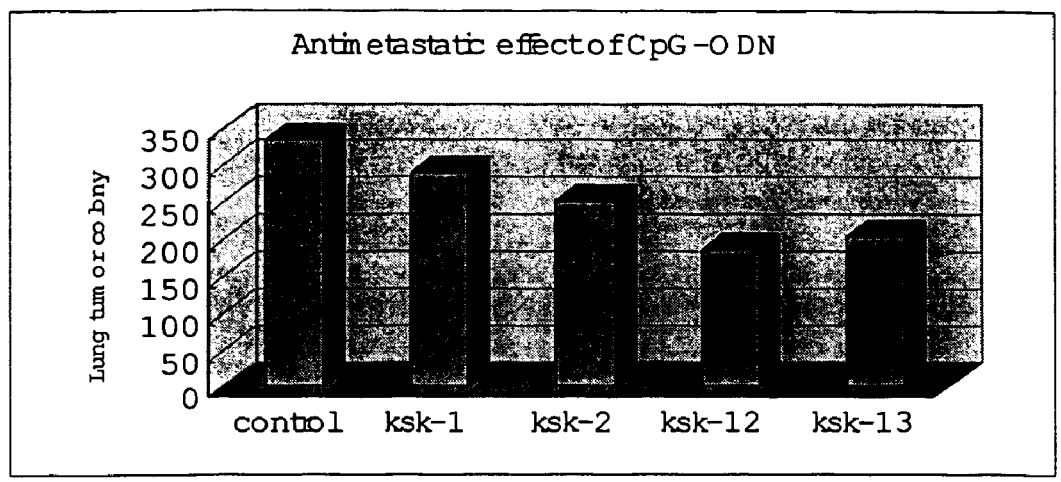
Figure 8A:
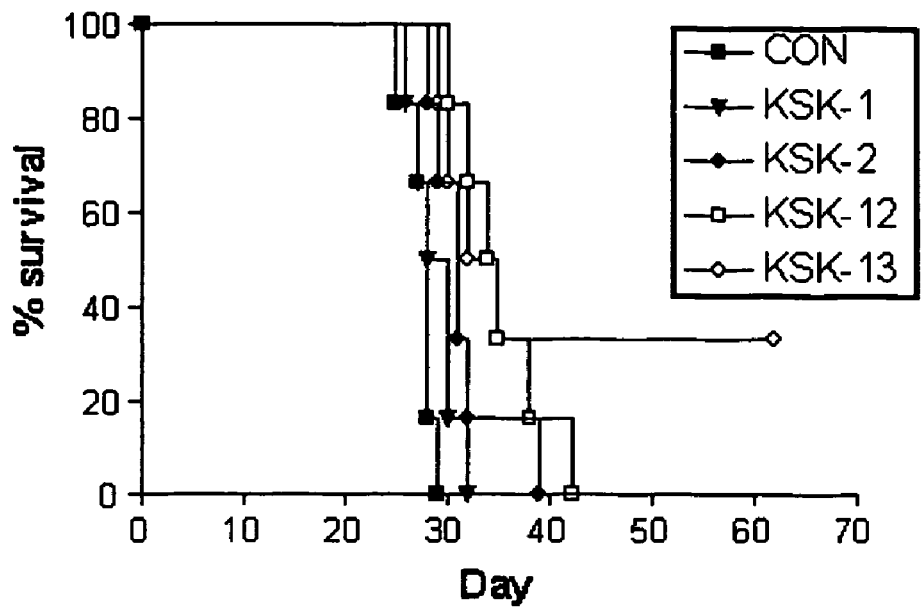
Figure 8B:
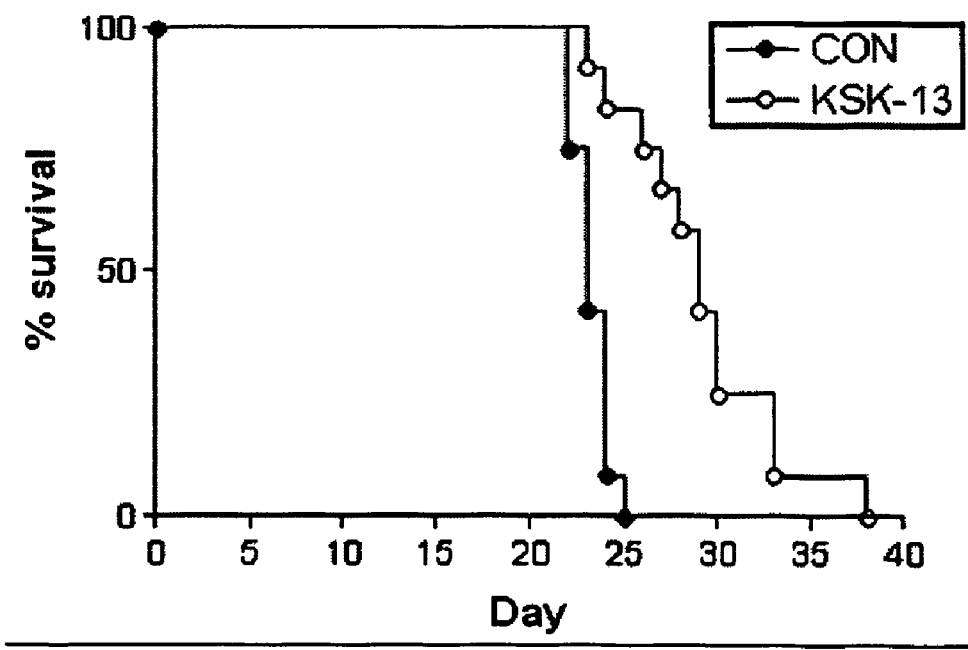
Figure 9:
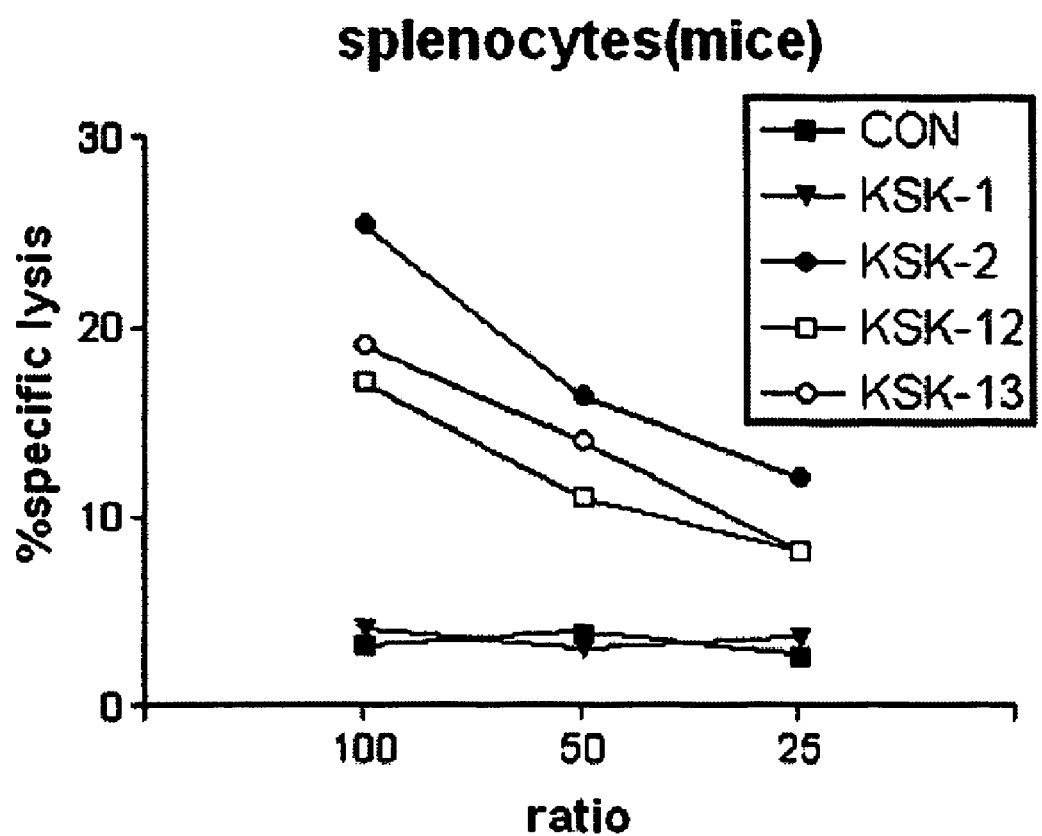

FIG. 4a shows the results of examining whether the CpG ODN of the present invention induces expression of B7.2 costimulatory molecule of mouse peritoneal macrophages;

FIG. 4b shows the results of examining whether the CpG ODN of the present invention induces expression of MHC Class I molecule in mouse peritoneal macrophages;

FIG. 5a shows the results of examining whether the CpG ODN of the present invention induces expression of B7.2 costimulatory molecule in mouse splenocytes;

FIG. 5b shows the results of examining whether the CpG ODN of the present invention induces expression of MHC Class I molecule in mouse splenocytes;

FIG. 6a shows the lysis level of YAC-1 cell susceptible to a natural killer cell when cytotoxicity of the natural killer cell contained in splenocytes is augmented by treating the splenocytes with the CpG ODN of the present invention;

FIG. 6b shows the lysis level of K562 cell susceptible to a natural killer cell when cytotoxicity of the natural killer cell contained in human peripheral blood mononuclear cells is augmented by treating the human peripheral blood mononuclear cells with the CpG ODN of the present invention;

FIG. 7 shows lung metastasis inhibitory effect of the CpG ODN of the present invention on B16 melanoma tumor bearing mice;

FIG. 8a shows the results of comparing survival prolongation effects of various CpG ODNs on EL4 metastasized-C57BL/6 mice;

FIG. 8b shows the results of the survival prolongation effects of KSK-13 CpG ODN on EL4 metastasized-C57BL mice: and FIG. 9 shows the results of cytotoxicity of natural killer cells which are activated by the CpG ODN of the present invention.

DETAILED DESCRIPTION OF THE INVENTION

The present invention provides a modified CpG ODN showing immunoactivity and containing a CpG motif, wherein a consecutive sequence of dT is coupled to the 3'-terminus of ODN.

Further, the present invention provides a use of the modified CpG ODN as a vaccine adjuvant or an anti-cancer agent.

Hereinafter, the present invention is described in detail.

The present invention relates to the modified CpG ODN which is prepared by coupling a consecutive sequence of dT to the 3'-terminus of CpG ODN having immunoregularory function, leading to improve the immunoactivity of splenocytes, macrophages and peripheral blood mononuclear cells, and therefore, can be effectively used as a vaccine adjuvant for preventing and treating hepatitis B or an anti-cancer agent.

Hereinafter, the term "ODN" means an oligodeoxynucleotide having 11 to 26 nucleotides in length which is capable of activating an immune response. In particular, the term "CpG ODN" means an oligodeoxynucleotide having a CpG motif (5'-purine purine CpG pyrimidine pyrimidine-3') which shows immunoregularory function. The term "a consecutive sequence of dT" means a form of successively coupling at least 4 deoxyribothymines to the CpG ODN by a phosphodiester bond.

The CpG ODNs used in the present invention are artificially synthesized by MetaBion (Germany), wherein all phosphodiester bonds are replaced by phosphorothioate bonds. After the synthesized CpG ODNs are subjected to HPLC (high-pressure liquid chromatography) and NAP purification procedures to maintain high purity, they are provided in a freeze-dried state. The nucleotide sequences of the CpG ODNs used in the present invention are shown in Table 1.

TABLE 1

| Name | SEQ ID No (Code name) | Nucleotide sequence (5' to 3') |
|---|---|---|
| 1982 | 1 (KSK-1) | TCCAGGACTTCTCTCAGGTT |
| 1826 | 2 (KSK-2) | TCCATGACGTTCCTGACGTT |
| 2006fG6run | 3 (KSK-7) | TCGTCGTTTTGTCGTTTTGTCGTTGGGGGG |
| 2006 | 4 (KSK-12) | TCGTCGTTTTGTCGTTTTGTCGTT |
| 2006f | 5 (KSK-13) | TCGTCGTTTTCGTCGTCGTTTT |

When a backbone of the ODN is formed by a natural phosphodiester bond, it can easily degraded by an attack of in vivo nuclease. In order for the CpG ODN with anti-cancer immunoactivity to exhibit a proper immunological effect, it is essential to increase its dose or modify its structure to avoid the above-mentioned attack by a nuclease. The CpG ODN of the present invention has a structure where its backbone is formed by a phosphorothioate bond, thus avoiding nuclease's attack while extending its in vivo half-life. However, a safety problem, when CpG ODN is administered in vivo, may be occurred in a non-specific immune response caused by the phosphorothioate bond itself. Thus, the present inventors examined the safety of the phosphorothioate bond by administering 50 μg of the CpG ODN having the phosphorothioate bond, pre-treated with aluminum hydroxide, along with other antigen such as gDE2t derived from CHO cell into a mouse. The result showed that there was no abnormal finding such as granuloma and necrosis at the injection site of the mouse, thus proving the safety of CpG ODN having the phosphorothioate bond.

The CpG ODN of the present invention activates myeloid lineaged cells to secrete proinflammatory and Th1 type cytokines, and eventually augments anti-cancer immunity. CpG ODN candidates were selected by primary screening using myeloid cell lines such as U-937, RAW264.7 and THP-1. Since the above cell lines may elicit a different immune response from primary cell lines to be targeted by the CpG ODN of the present invention, the inventors of the present invention examined the impact of the CpG ODN of the present invention on fresh murine splenocytes and peritoneal macrophages. The result showed that the CpG ODN significantly enhanced the levels of TNF-α, IL-6, IL-12 and IFN-γ mRNA expression and upregulated expression of MHC class II and B7.2 proteins on the surface of macrophages. These results showed that the CpG ODN of the present invention has a superior anti-cancer immunoactivity as compared with the activity of control natural killer cells present in mouse splenocytes and human peripheral blood mononuclear cells.

Accordingly, the CpG ODN of the present invention can be effectively used as a vaccine adjuvant, in particular, for preventing and treating hepatitis B. Here, it is preferable to administer an antigen for inducing an immune response and the CpG ODN twice or three times at intervals of from 2 to 4 week with a dose of ranging from 50 to 5,000 μg/kg body weight, respectively. Further, the ratio of the CpG ODN to the antigen is preferable to be in the range of from 5:1 to 4:1. The antigen may be immunized alone or together with aluminum hydroxide as a pharmaceutically acceptable vaccine adjuvant, and can be administered via an intramuscular injection or a subcutaneous injection.

The following Examples are given for the purpose of illustration only, and they should not be construed as limiting the scope of the present invention.

EXAMPLES

Example 1

Preparation of CpG ODN Having a Consecutive Sequence of dT at 3'-Terminus

CpG ODNs used in the present invention are artificially synthesized by MetaBion (Germany), wherein all phosphodiester bonds were replaced with phosphorothioate bonds. The synthesized CpG ODNs provided to us was in a freeze-dried state which went through HPLC (high-pressure liquid chromatography) and NAP purification procedures to maintain high purity. The nucleotide sequences of the CpG ODNs used in the present invention are shown in Table 1.

Example 2

Effect of CpG ODN on Proliferation of Mouse Splenocytes and Macrophages

The CpG ODNs synthesized in Example 1, which are expected to have anti-cancer immunoactivity, and the CpG ODNs, which have been already confirmed to have anti-cancer immunoactivity, were investigated whether they can induce cell proliferation when they are applied to mouse splenocytes and peritoneal macrophages, respectively, according to the following experiment.

1.5 ml of 3% thioglycholate was injected into a peritoneal cavity of BALB/C mouse. After 3 days of the injection, peritoneal cavity of the mouse was washed with a phosphate buffer solution supplemented with 2% fetal bovine serum and then collected. After washing further with Hanks' Buffered Salt Solution (HBSS) buffer solution twice, mouse peritoneal cavity macrophages were prepared in Dulbecco's Modification of Eagle's Medium (DMEM) supplemented with 10% fetal bovine serum.

Spleen was extracted from BALB/C mouse, homogenized into a unit of monocyte, centrifuged at 2,000 rpm for 5 min and its supernatant was discarded. A cell pellet was mixed with 0.84% ammonium chloride for lysis of red blood cells and washed with RPMI 1640 twice to obtain mouse splenocytes.

inventors investigated the mRNA expression of the proinflammatory or Th1 type cytokine release induced by KSK-13. These cytokines may contribute to anti-cancer immune defense. The detailed experimental methods are as follows.

Mouse peritoneal macrophages were prepared same as in Example 2. $1\times10^6$ cells of macrophages were treated with 0.6 μg/ml of CpG ODN for 12 hrs. Total RNA was isolated from the treated cells using TRIzol® reagent (Life Technology), and its concentration was determined by measuring its absorbance. RT-PCR was carried out to synthesize cDNA using MMLV reverse transcriptase (Promega) with 1 μg of the total RNA as a template RNA. Then, PCR was conducted using the synthesized cDNA as a template according to the reaction conditions in Table 2 to amplify TNF-$\alpha$, IL-6, IL-12 and IFN-$\gamma$, respectively.

TABLE 2

| | TNF-$\alpha$ | | IL-6 | | IL-12 | | IFN-$\gamma$ | |
|---|---|---|---|---|---|---|---|---|
| Reaction Conditions | 95° C., 5 min | 1 cycle | 95° C., 5 min | 1 cycle | 95° C., 5 min | 1 cycle | 95° C., 5 min | 1 cycle |
| | 95° C., 50 sec | 30 cycle | 95° C., 50 sec | 35 cycle | 95° C., 60 sec | 30 cycle | 95° C., 50 sec | 33 cycle |
| | 53° C., 50 sec | | 55° C., 60 sec | | 65° C., 60 sec | | 60° C., 50 sec | |
| | 72° C., 90 sec | | 72° C., 90 sec | | 72° C., 120 sec | | 72° C., 90 sec | |
| | 72° C., 8 min | 1 cycle | 72° C., 8 min | 1 cycle | 68° C., 8 min | 1 cycle | 72° C., 8 min | 1 cycle |

After $5\times10^4$ cells of the splenocytes and macrophages prepared above were treated with 0.6 μg/ml each of KSK-1, KSK-2, KSK-7, KSK-12 and KSK-13, and 0.1 μg/ml of LPS for 24, 48 and 72 hrs, respectively, they were cultured in RPMI 1640 supplemented with [$^3$H] thymidine for 6 hrs. The activated splenocytes were allowed to take in [$^3$H] thymidine from the medium during their proliferation. After removing the medium, the splenocytes were washed with the same medium without [$^3$H] thymidine, and the amount of [$^3$H] thymidine taken by the splenocytes was measured using a radiation detector.

Figure 1:
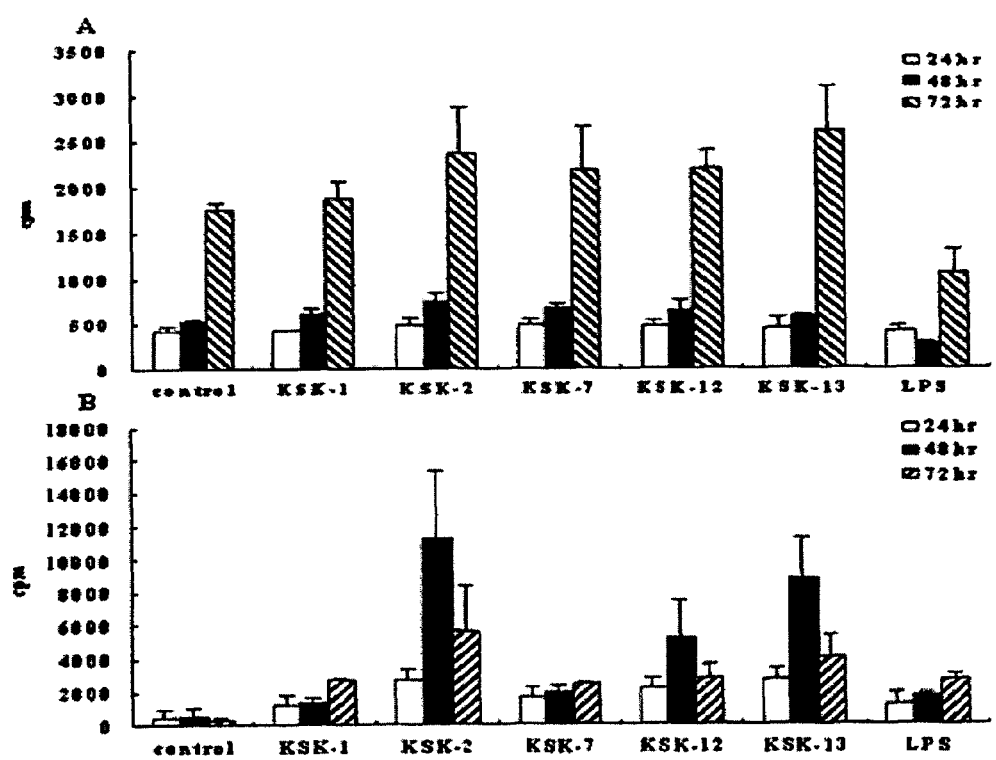
FIG. 1 shows the results of examination whether the CpG ODN of the present invention induces proliferation of BALB/C mouse macrophages (A) and splenocytes (B) in vitro.

In (A) of FIG. 1, the CpG ODNs were treated for 72 hrs in order to induce the proliferation of macrophages. KSK-13 among them showed higher proliferation than other CpG ODNs including KSK-2 known as inducing the highest immunoactivity, and also showed a statistically significant effect for inducing proliferation as compared with that of a control (no treatment) or KSK-1, a non-CpG ODN.

Further, as shown in (B) of FIG. 1, the effect of CpG ODN of the present invention for inducing proliferation of mouse splenocytes was significantly greater than that of other CpG ODNs for mouse macrophages. In order to induce proliferation of splenocytes, the splenocytes were treated with the CpG ODN for 48 hrs. When the CpG ODN was treated for 72 hrs, the proliferation level of splenocytes was decreased. The effect of KSK-13 for inducing proliferation of splenocytes showed a slightly lower mean value than that of KSK-2, which is known effective in a mouse, but the difference was statistically insignificant.

Example 3

Effect of CpG ODN on Th1 Type Cytokine mRNA Expression of Mouse Peritoneal Macrophages Based on that KSK-13 can induce proliferation of mouse peritoneal macrophages as shown in Example 2, the present The resulting PCR products were analyzed on a 1% agarose gel to compare the expression levels of each cytokine mRNA under each reaction condition.

Further, β-Actin, a constituitively expressed protein, was used as a control to confirm whether a constant level of PCR products are obtained in the above PCR reaction conditions and the result showed that an equal level of PCR products were obtained in each reaction condition thus showing that the difference in thickness of PCR products visualized on the gel was not due to a procedural error in cDNA preparation.

Figure 2A:
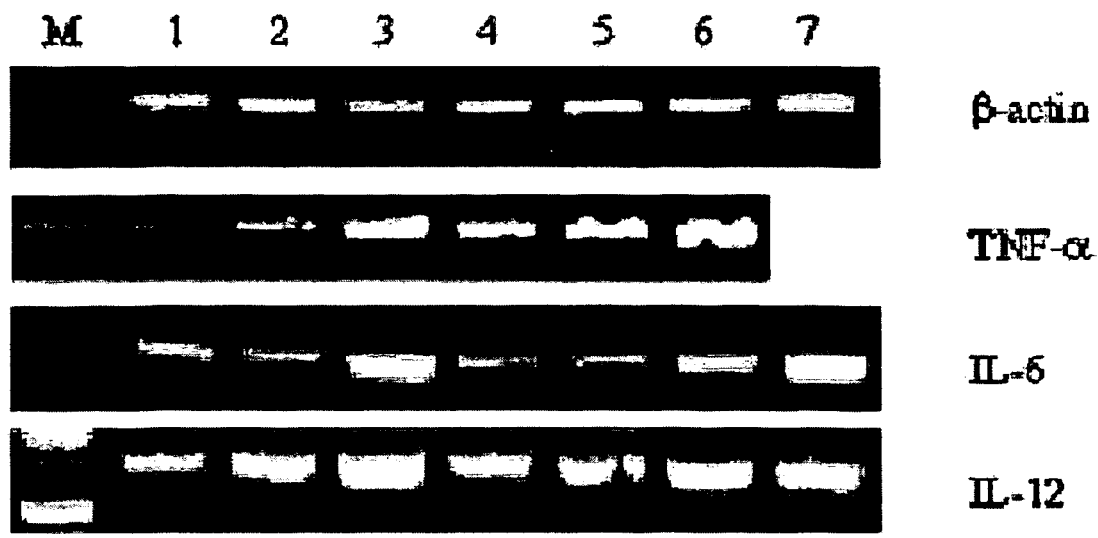
FIG. 2a shows the results of examination whether the CpG ODN of the present invention induces expression of Th1 type cytokine mRNA of Balb/c mouse peritoneal macrophages in vitro.
Figure 2B:
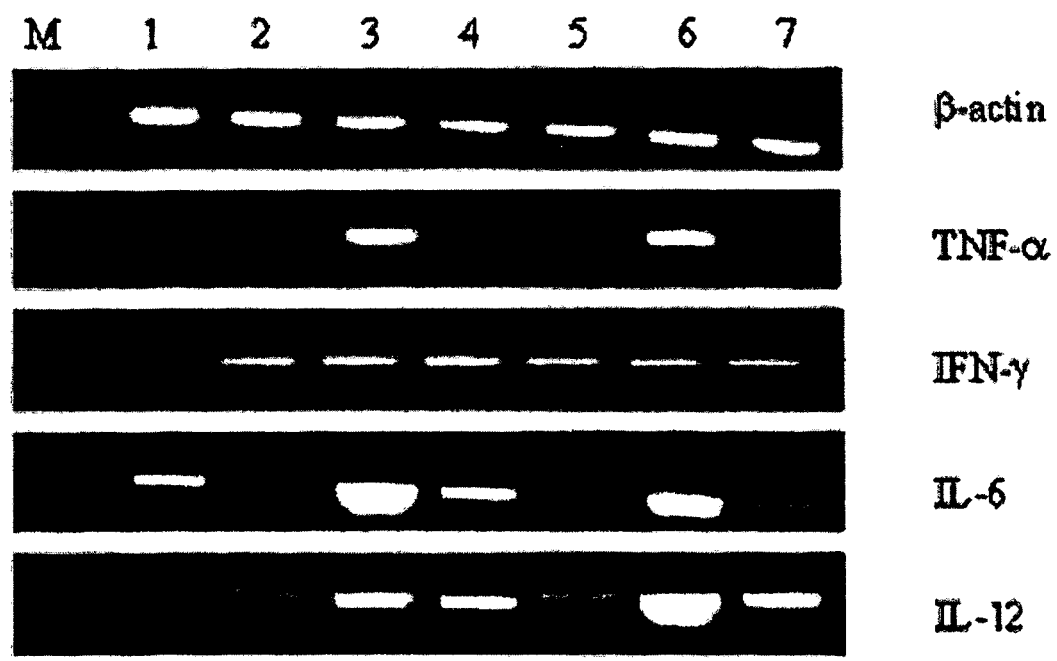
FIG. 2b shows the results of examining whether the CpG ODN of the present invention induces expression of Th1 type cytokine mRNA of BALB/C peritoneal macrophages in vivo.

As shown in FIG. 2a, KSK-13 increased the levels of TNF-$\alpha$, IL-6 and IL-12 mRNA expression in vitro, similar to KSK-2 which highly activates immunocytes of a mouse. This difference became greater in vivo thus suggesting that KSK-13 exerts anti-cancer immunoactivity under in vivo condition (FIG. 2b).

Example 4

Effect of CpG ODN on Th1 Type Cytokine mRNA Expression of Mouse Splenocytes

It was found that KSK-13 can induce proliferation of mouse splenocytes in Example 2. Thus, the present inventors investigated the amount of cytokine secretion induced by KSK-13 which is involved in anti-cancer immunity in these cells as follows.

Mouse splenocytes were prepared same as in Example 2. $1\times10^6$ cells of splenocytes were treated with 0.6 μg/ml of CpG ODN for 12 hrs. Total RNA was isolated from the treated cells using TRIzol® reagent (Life Technology), and its concentration was determined by measuring its absorbance. RT-PCR was carried out to synthesize cDNA using MMLV reverse transcriptase (Promega) with 1 μg of the isolated RNA as a template. Then, PCR was conducted using the synthesized cDNA as a template according to the reaction conditions described in Table 2, to amplify TNF-α, IL-6, IL-12 and IFN-γ, respectively.

PCR products were analyzed on a 1% agarose gel to compare the levels of each cytokine mRNA expression under each reaction condition.

Further, β-Actin, a constituitively expressed protein, was used as a control to confirm whether a constant level of PCR products are obtained in the above PCR reaction conditions and the result showed that an equal level of PCR products were obtained in each reaction condition thus showing that the difference in thickness of PCR products visualized on the gel was not due to a procedural error in cDNA preparation.

As shown in FIG. 3a, KSK-13 increased the levels of TNF-α, IL-6 and IL-12 mRNA expression in the splenocytes in vitro, similar to KSK-2 which highly activates immunocytes of a mouse. This difference became greater in vivo, thus suggesting that KSK-13 exerts anti-cancer immunoactivity under in vivo condition (FIG. 3b).

Example 5

Effect of CpG ODN on Expression of Signal Transfer Molecule of Mouse Peritoneal Macrophages To investigate whether KSK-13 capable of activating mouse peritoneal macrophages in vitro can also activate them in vivo, the following experiment was carried out.

The CpG ODN was injected into a peritoneal cavity of BALB/C mouse with 3% thioglycolate. After 48 hrs of the injection, mouse peritoneal macrophages were prepared same as in Example 2. The cells were labeled with FITC-conjugated anti-B7.2 monoclonal antibody or anti-MHC class II monoclonal antibody and analyzed using a flow cytometer. In FIG. 4, a control means a non-treatment group; KSK-1, KSK-2, KSK-7, KSK-12 and KSK-13 were treated at a concentration of 0.6 μg/ml, respectively; and LPS was treated at a concentration of 0.1 μg/ml.

B7.2 molecule is a supplementary stimulating molecule whose expression level is increased when macrophages are activated. In case of the non-treatment group, the expression level of B7.2 molecule in the peritoneal macrophages was 2.9% within the standard deviation, but that of KSK-13 of the present invention was 14.2%. This was an activation rate similar to the expression level of the typical mouse CpG ODN, KSK-2 (i.e., 16.3%), or that of the human CpG ODN, KSK-12 (i.e. 17.3%), and significantly different from that of the non-CpG ODN, KSK-1 (i.e., 5.1%) (FIG. 4a).

MHC class II molecule plays a key role in antigen presentation of macrophages, and its expression level becomes increased together with B7.2 molecule when macrophages are activated. In the non-treatment group, the expression level of MHC class II molecule in the peritoneal macrophages was 26.5% within the standard deviation, but that of KSK-13 of the present invention was 33.7%. This was an activation rate similar to the expression level of the typical mouse CpG ODN, KSK-2 (i.e. 35.8%), or that of the human CpG ODN, KSK-12 (i.e. 30.2%), and significantly different from that of the non-CpG ODN, KSK-1 (i.e., 25.0%) (FIG. 4b).

Given these results, it was found that KSK-13 of the present invention could activate mouse peritoneal macrophages in vivo. The increase in the expression levels of MHC class II and B7.2 molecules indicate that an antigen presentation ability of peritoneal macrophages was activated, which proved the effect of KSK-13 as an immune enhancing agent.

Example 6

Effect of CpG ODN on Expression of Signal Transfer Molecule of Mouse Splenocytes To investigate whether KSK-13 capable of activating mouse splenocytes in vitro can also activate them in vivo, the following experiment was carried out.

The CpG ODN was injected into a peritoneal cavity of BALB/C mouse with 3% thioglycolate. After 48 hrs of the injection, mouse splenocytes were prepared same as in Example 2. The cells were labelled with FITC-conjugated anti-B7.2 monoclonal antibody or anti-MHC class II monoclonal antibody and analyzed using a flow cytometer.

In case of the non-treatment group, the expression level of B7.2 molecule in the splenocytes was 2.8% within the standard deviation, but that of KSK-13 of the present invention was 8.6%. This was lower than the expression level of the typical mouse CpG ODN, KSK-2 (i.e. 12.13%), but higher than that of the human CpG ODN, KSK-12 (i.e. 6.85%). Further, it was significantly different from the expression level of the non-CpG ODN, KSK-1 (i.e., 3.31%) (FIG. 5a).

Further, in case of the non-treatment group, the expression level of MHC class II molecule in the splenocytes was 15.5% within the standard deviation, but that of KSK-13 of the present invention was 22.8%. This was similar to the expression level of the typical mouse CpG ODN, KSK-2 (i.e. 23.6%), higher than that of the human CpG ODN, KSK-12 (i.e. 18.6%), and significantly different from that of the non-CpG ODN, KSK-1 (i.e., 17.5%) (FIG. 5b).

These results suggested that KSK-13 of the present invention can activate mouse splenocytes in vivo. The increase in the expression levels of MHC class II and B7.2 molecules indicate that an antigen presentation ability of B cell among the splenocytes was activated, thus showing the effect of KSK-13 as a potent immunostimulant.

Example 7

Effect of CpG ODN on Immunization of a Mouse with Hepatitis B Surface Antigen

To investigate whether KSK-13 capable of activating mouse splenocytes and peritoneal macrophages can act as a vaccine adjuvant when a mouse is immunized with hepatitis B surface antigen, the following experiment was carried out.

Thirteen experimental groups were constituted and 7 BALB/C mice were assigned to each group. Each mouse was subcutaneously injected at the abdominal region with 2.5 μg hepatitis B surface antigen together with a vaccine adjuvant as described in Table 3. After the immunization was repeated twice at 1-week intervals according to the same method described above, blood was collected. A titer of anti-hepatitis B surface antigen antibody was determined by indirect enzyme linked immunosorbent assay using the blood, and the results are shown in table 3.

TABLE 3

| Experimental group | Adjuvant | Anti-HBsAgAb (IgG) |
|---|---|---|
| 1 | No antigen | 0 |
| 2 | No adjuvant | 200 |
| 3 | Alum | 200 |
| 4 | KSK-1 | 800 |
| 5 | KSK-2 | 12,800 |
| 6 | KSK-7 | 800 |

TABLE 3-continued

| Experimental group | Adjuvant | Anti-HBsAgAb (IgG) |
|---|---|---|
| 7 | KSK-12 | 12,800 |
| 8 | KSK-13 | 12,800 |
| 9 | KSK-2 + alum | 3,200 |
| 10 | KSK-12 + alum | 12,800 |
| 11 | KSK-13 + alum | 51,200 |
| 12 | CFA* | 12,800 |
| 13 | CFA + alum | 3,200 |

The titer was 800 in case of single immunization of hepatitis B surface antigen, but it was increased 16-fold higher (12,800) when KSK-1, KSK-12 and KSK-13 were co-administered with recombinant HBs Ag, respectively. When injected together with alum, which has been widely used in clinical trials, the effect of KSK-13 as a vaccine adjuvant was 4-fold higher than that of KSK-12 and 64-fold higher than that of KSK-2. Further, this effect of KSK-13 was equal to that of CFA (Complete Freund's Adjuvant). These results suggested that KSK-13 can be effectively used as a vaccine adjuvant with peptide antigen.

Example 8

Effect of CpG ODN on Anti-Cancer Activity of Mouse Splenocytes

To investigate whether KSK-13 capable of activating mouse splenocytes and peritoneal macrophages can activate the ability of natural killer cells for removing cancer cells included in splenocytes, the following experiment was carried out.

A phosphate buffer solution (control), or 10 µg of KSK-2, KSK-12 or KSK-13 was injected at a peritoneal cavity of BALB/C mouse. After 18 hrs injection, a spleen was ablated from the mouse and splenocytes were prepared therefrom. The splenocytes were incubated in a culture plate for 2 hrs to be adhered to the wall, and free cells (non-adherent cells) were transferred to a new culture plate. The cells were treated with 1.0 µg/ml of the same kind of CpG ODN for 2 hrs, and then, co-incubated with $5 \times 10^3$ cells of $^{51}$Cr-labeled YAC-1 cells at a ratio shown in FIG. 6. A supernatant was taken from the culture solution and the amount of $^{51}$Cr eluted into the solution was measured by using a gamma counter.

FIG. 6a shows the lysis level of YAC-1 cell susceptible to a natural killer cell when cytotoxicity of the natural killer cell included in splenocytes was increased by treating the splenocytes with KSK-13. Non-adherent splenocytes (effector cell, E) and YAC-1 cells (target cell, T) were mixed at a ratio of 100:1, 50:1, 25:1 and 12:1, respectively. In case of the control, although the number of effector cells was increased up to the range from 12-fold to 100-fold higher than that of target cells, the lysis level of target cell was not significant. In contrast, in case of KSK-13, the lysis level of target cell increased up to about 3.5% as the number of effector cells were increased. This was lower than the lysis level of the typical mouse CpG ODN, KSK-2, but higher than that of the human CpG ODN, KSK-12.

FIG. 6b showed the lysis level of K562 cell susceptible to a natural killer cell. In the concrete, cytotoxicity of the natural killer cell included in human peripheral blood mononuclear cells (PBMC) was markedly augmented by treating the human PBMC with the CpG ODN of the present invention. Human PBMC were prepared as follows. Blood was collected from a healthy volunteer in a heparin-coated test tube and centrifuged at 1,200 g for 10 min. After a boundary layer region was harvested therefrom and transferred to a new tube, it was diluted with an equal volume of an isolating buffer solution (phosphate buffer solution containing 0.5% fetal bovine albumin and 1 mM EDTA). An equal volume of Histopaque-1077 (Sigma) was poured into a new tube and the diluent was gently added thereon. The tube was centrifuged at 1,200 g for 30 min. Peripheral mononuclear cells at the boundary layer were collected in a new tube and resuspended in the isolating buffer solution. The suspension was centrifuged at 210 g for 5 min to discard a supernatant. The procedure was repeated three times.

The prepared peripheral mononuclear cells (effector cell, E) were mixed with K562 cells (target cell, T) at a ratio of 50:1, 25:1 and 12:1 and cultured, respectively. In case of the control and KSK-13, when they were mixed at a ratio of 25:1 and cultured, cytotoxicity of natural killer cells included in the peripheral blood mononuclear cells treated with KSK-13 already reached 65%, but that of the control was only about 9%. Why there was little difference in cytotocixity between the mixing ratio of 50:1 and 25:1 was because that cytotoxicity was sufficiently induced at the mixing ratio of 25:1. Further, the results of FIGS. 6a and 6b suggested that KSK-13 may be more effective in humans than in mice.

Example 9

Anti-Cancer Activity

1) Effect on Inhibiting B16 Melanoma Lung Metastasis

All B16 melanoma cells were cultured in RPMI 1640 supplemented with 10% heat-inactivated FBS. $2 \times 10^5$ melanoma cells (0.2 mL PBS) were injected into the lateral tail vein of mice (Specific pathogen-free 7-8 week-old female C57BL/6) I.V. Each CpG (10 µg/mice) was administered into I.P. for treatment of B16 metastasized mice (Day of Treatment: $1^{st}$, $3^{rd}$, $5^{th}$, $7^{th}$ and $9^{th}$ day) (FIG. 7).

2) Effect of Prolonging the Survival Rate of Mouse by Inhibiting Local Metastasis of Cancer Cells EL4 cells (T cell lymphoma, $2 \times 10^4$) were intravenously injected to 6 C57BL/6 mice per each group to inoculate cancer cells. At 1, 3, 5, 7 and 9 days after the injection, KSK-13 (10 µg/mouse) was injected at a peritoneal cavity of BALB/C mouse and survival rate of each mouse was estimated. KSK-13 prolonged the survival rate of all 6 mice, in particular, 2 of them survived after 60 days (FIG. 8a).

Further, this effect of KSK-13 for prolonging the survival rate was repeatedly confirmed in the experiment using only KSK-13 CpG ODN with increasing the number of mice (FIG. 8b).

3) Cytotoxicity of Natural Killer Cells Activated by CpG ODN

Monocytes were removed from human peripheral blood mononuclear cells by negative selection and only B, T and natural killer cells were used in the following experiment. Non-adherent cells except for macrophages were separated from the mouse splenocytes and used as effector cells. As a target cell working on natural killer cells specifically, K562 cell line was used for measurement of human NK (natural killer) cell cytotoxicity whereas YAC-1 cell line was used for that of murine NK cell cytotoxicity. Cytotoxicity of natural killer cells was measured by $^{51}$Cr release assay using the above effector and target cells (FIG. 9).

Example 10

Toxicity Test 0.5 mg of KSK-13 was intramuscularly injected into gluteus maximus or a deltoid muscle in six ICR mice. Two mice were injected with KSK-13 twice at 2-week intervals. One of them was further injected three additional times with KSK-13 at 2-week intervals after one month from the primary injection.

After injection, mice were observed with regard to clinical signs, physical examinations such as body weight and body temperature, haematology and urinalysis for the period of 6 months. The results showed that all tested animals survived, and there were no striking aberrant clinical signs, changes in weights or other toxic effects.

Preparation Example 1

Preparation of Vaccine 1 mg of hepatitis B surface antigen, 10 mg of dT-labeled oligodeoxynucleotide of the present invention, 1 mg of aluminum hydroxide, 0.01 w/v % of thimerosal, a proper dose of potassium dihydrogen phosphate and sodium hydrogen phosphate as a buffering agent and an appropriate dose of sodium chloride were mixed in distilled water and the mixture's pH was adjusted with hydrochloric acid to prepare a vaccine.

While the embodiments of the subject invention have been described and illustrated, it is obvious that various changes and modifications can be made therein without departing from the spirit of the present invention which should be limited only by the scope of the appended claims.

---

What is claimed is:

1. A structurally modified oligodeoxynucleotide (ODN) consisting of the nucleotide sequence of SEQ ID NO: 5 having immunoactivity and a CpG motif, wherein the ODN has a consecutive sequence of 4 deoxyribothymines (dT) at the 3'-terminus of ODN, which is modified by changing the phosphodiester bonds into phosphorothioate bonds.

2. A structurally modified oligodeoxynucleotide (ODN) comprising the nucleotide sequence of SEQ ID NO: 5 having immunoactivity and a CpG motif, wherein the ODN has a consecutive sequence of at least 4 deoxyribothymines (dT) at the 3'-terminus of ODN, which is modified by changing the phosphodiester bonds into phosphorothioate bonds.

3. The oligodeoxynucleotide of claim 1 or 2, wherein the ODN increases immunoactivity of splenocytes, macrophages or peripheral blood mononuclear cells.

4. A vaccine adjuvant comprising the oligodeoxynucleotide of claim 1 or 2 as an effective ingredient.

5. The vaccine adjuvant of claim 4, further comprising an antigen.

6. The vaccine adjuvant of claim 4, which is used for treating hepatitis B.

7. The vaccine adiuvant of claim 5, which is used for treating hepatitis B.

* * * * *